United States Patent [19]

Alburger

[11] 4,090,402
[45] May 23, 1978

[54] SLOW-SOLUBILITY INSPECTION PENETRANT COMPOSITION CONTAINING A SOLUBILITY ACCELERATOR

[76] Inventor: James R. Alburger, 5007 Hillard Ave., La Canada, Calif. 91011

[21] Appl. No.: 808,136

[22] Filed: Jun. 20, 1977

[51] Int. Cl.² ............... G01N 21/16; C09K 11/06; C09K 3/00
[52] U.S. Cl. ............... 73/104; 252/301.19; 252/408
[58] Field of Search ............ 73/104; 252/408, 301.2 P

[56] References Cited

U.S. PATENT DOCUMENTS

| | | | |
|---|---|---|---|
| Re. 28,605 | 11/1975 | Alburger | 73/104 |
| 2,667,070 | 1/1954 | Sockman et al. | 73/104 |
| 2,839,918 | 6/1958 | Switzer | 73/104 |
| 3,415,112 | 12/1968 | Alburger | 73/104 |
| 3,543,570 | 12/1970 | Mlot-Fijalkowski | 252/408 |
| 3,558,882 | 1/1971 | Mlot-Fijalkowski | 252/408 |
| 3,751,970 | 8/1973 | Alburger | 73/104 |
| 3,896,664 | 7/1975 | Alburger | 252/408 |
| 3,926,044 | 12/1975 | Alburger | 73/104 |
| 3,929,664 | 12/1975 | Alburger | 252/408 |
| 4,037,466 | 7/1977 | Alburger | 73/104 |

Primary Examiner—Benjamin R. Padgett
Assistant Examiner—T. S. Gron

[57] ABSTRACT

An inspection penetrant process and composition therefor in which the penetrant is formulated from a low-solubility liquid, and a solubility accelerator material is added to the formulation to enhance the washability of the penetrant to provide for more rapid removal of background porosity entrapments from test surfaces. The acceleration of solubility is accomplished while the features of slow-solubility and adaptability to recovery and re-cycling procedures are retained.

1 Claim, No Drawings

SLOW-SOLUBILITY INSPECTION PENETRANT COMPOSITION CONTAINING A SOLUBILITY ACCELERATOR

RELATED PATENTS

U.S. Pat. No. 3,896,664 — ENHANCED STABILITY WATER-WASHABLE PENETRANT COMPOSITION AND PROCESS.

U.S. Pat. No. 3,926,044 — CLOSED-LOOP WATER-WASHABLE INSPECTION PENETRANT PROCESS.

U.S. Pat. No. 3,927,551 — FRACTURED GLASS TESTING PANEL FOR DYED LIQUID PENETRANTS.

U.S. Pat. No. 3,929,664 — WATER-WASHABLE INSPECTION PENETRANT EMPLOYING TRIGLYCERIDES AND POLYGLYCERIDES OF FATTY ACIDS.

U.S. Pat. No. 3,930,407 — WATER-WASHABLE INSPECTION PENETRANT EMPLOYING MINERAL SOLVENT AND A FATTY ACID SOLUBILITY PROMOTER.

U.S. Pat. No. 3,931,733 — METHOD AND MEANS OF ACCELERATING REMOVAL OF BACKGROUND ENTRAPMENTS IN THE INSPECTION PENETRANT PROCESS.

U.S. Pat. No. 3,948,092 — METHOD OF RECOVERING AND RE-CYCLING WATER-WASHABLE INSPECTION PENETRANTS.

U.S. Pat. No. 3,978,717 — INHIBITED PRE-WASH STRIPPER COMPOSITION FOR WATER-WASHABLE INSPECTION PENETRANTS.

This invention relates to inspection penetrant materials. More particularly, the invention relates to water-washable inspection penetrant compositions which exhibit enhanced values of indication stability in the presence of wash water.

Heretofore, water-washable inspection penetrants have been comprised essentially of a water-dispersible liquid carrier containing a dissolved indicator dye. The liquid penetrant composition is selected or formulated so as to be readily soluble or self-emulsifiable in water. The indicator dye may be a visible-color dye or a fluorescent dye, but for highsensitivity usage fluorescent dyes are most generally utilized.

In use, the water-washable penetrant is applied to parts to be tested for the presence of surface flaws. After a suitable dwell time, during which the penetrant enters any surface cracks which are present, the test parts are washed with water to remove surface penetrant, leaving entrapments of the tracer-dyed liquid in the surface cracks. Following the wash-removal step, the test parts are dried and sometimes they are treated with a fine-powder developer which acts to draw out penetrant entrapments to a point where they can be seen. In any event, the parts are inspected for the presence of surface-flaw indications, using white light in the case of a penetrant containing visiblecolor dye, or under black light in the case of a penetrant containing a fluorescent dye or dyes. Entrapments of dyed penetrant which are retained or developed on a coating of powder particles are detected by their visible color or fluorescence, as the case may be. Normally, the step of development is considered to be part of the inspection step in the process.

In the past, it has been the practice to formulate water-washable penetrants in such a way that the compositions exhibit a feature of "good washability", such that the surface penetrant is easily removed when test parts are washed with water. Acceptable penetrant formulations have apparently been chosen for their ability to wash quickly so as to provide a relatively clean test surface with a minimum background or residues of dye penetrant. I have discovered that existing water-washable penetrants suffer from a serious drawback, in that they are characterized by an excessive degree of solubility or emulsifiability, such that in the process of wash-removal of surface penetrant, entrapments of penetrant in small, shallow surface flaws are also removed, or are at least depleted to an excessive degree.

I have devised various means whereby the retention of penetrant entrapments in flaws may be improved. For example, I have devised the so-called gel-forming penetrants as exemplified by the teachings of my U.S. Pat. Nos. 3,282,843, 3,349,041, and 3,429,826, and my copending application Ser. No. 127,681, filed Mar. 24, 1971, for "Inspection Penetrant Composition and Process Employing Balanced Surfactant/Synergist Detergent Systems".

I have also devised various methods of inhibiting the solubility of certain kinds of penetrants (particularly the gel-forming penetrants), by adjustment of the detergent balance of the composition, by introduction of certain solubility-inhibiting chemicals into the penetrant or into the wash water, or by raising the temperature of the wash water above a critical point of solubility inversion, as exemplified by the teachings of my U.S. Pat. No. 3,935,731.

In addition, I have devised the so-called slow-solubility penetrants, as exemplified by the teachings of my above-identified U.S. Pat. Nos. 3,896,664, 3,929,664, and 3,930,407. These so-called slow-solubility inspection penetrants have proved to be exceptional insofar as their ability to form highly stable flaw entrapments is concerned, and penetrants of this kind are also readily adaptable to recovery and re-cycling in accordance with my above-identified U.S. Pat. Nos. 3,926,044 and 3,948,092. In addition, they are adaptable to pre-wash recovery in accordance with the teachings of my above-identified U.S. Pat. No. 3,978,717.

The slow-solubility penetrants and processes therefor have presented a problem in that they provide flaw-entrapment efficiencies which are somewhat greater than is wanted for most industrial inspection usages. This means that the effective water-solubility of a penetrant formulated from the low-solubility liquids disclosed in the above-identified patents is not quite great enough to provide a satisfactory removal of certain kinds of porosity background indications.

In my above-identified U.S. Pat. No. 3,896,664, I have disclosed and claimed the use of certain solvent-couplers, such as alcohols and glycol-ethers, as solvency accelerators. Materials of the thus-described kinds act to interfere with the "Closed-Loop" recovery and re-cycling process which is described in my U.S. Pat. No. 3,926,044. This is because such ordinary solvent-couplers have a strong affinity for water and are selectively dissolved in the wash water in preference to the low-solubility liquid which is used in the slow-solubility penetrant formulation. The result is that the wash water cannot be readily clarified and purified for re-use.

There is therefore a need for a method and means of enhancing to a controlled degree the solubility characteristics of the slow-solubility penetrants, a means wherein the features of slow-solubility and adaptability to recovery and re-cycling procedures are retained.

The principal object of the invention, therefore, is to provide improved formulations of slow-solubility inspection penetrants in which the effective solubility in water is increased to a controlled degree.

Another object of the invention is to provide enhanced-solubility slow-solubility inspection penetrants in which features of slow-solubility and adaptability to procedures of recovery and re-cycling are retained.

These and other objects of the invention will in part be obvious and will in part become apparent from the following description thereof.

I have discovered that the various slow-solubility penetrant formulations which utilize low-solubility liquids may be modified so as to provide an enhanced degree of water-solubility by adding thereto a certain specified proportional amount of a solvency accelerator to be hereinafter identified. The solvency accelerator may be employed in amounts ranging from as little as 5 percent up to 100 percent (of the liquid vehicle), and will yield an effective acceleration of wash-removal of background indications such that such unwanted background indications may be reduced to as little as 5 to 10 percent of the levels which would be produced without the use of the accelerator.

I have found that any one or a combination of the following materials may be used as a solubility accelerator for a so-called slow-solubility inspection penetrant:
Ethylene glycol hexyl ether,
Diethylene glycol hexyl ether
Butoxy propanol
Cyclohexanol
Cyclohexanone
Methyl amyl alcohol
1-Pentanol
2-Methyl-1-butanol
Amyl alcohol
Ethylene glycol ethyl ether acetate
Ethylene glycol butyl ether acetate
Diethylene glycol butyl ether acetate
Glyceryl triacetate
Glycol diacetate
2-Ethyl-1,3-hexanediol
Methyl heptyl ketone
Polypropylene glycol (M.W. = 1200)
Diethyl maleate
Diethyl succinate Similar glycol-ether derivitives would also be useful for the purpose of the invention, such as propylene glycol hexyl ether, diethylene glycol phenyl ether, ethylene glycol phenyl ether, propylene glycol phenyl ether, and the like, provided that their solubility in water falls in the range of about 1% up to 10%. However, many of such glycol ethers are not commercially available at this time.

Some of the above-identified glycol-ethers and esters, alcohols, etc., are less desirable than others for the purpose of the invention, as for materials which have excessively low flash points or excessively high volatility. A preferred solubility accelerator material is diethylene glycol butyl ether acetate, since this substance has a flash point in the range of 240° F., a boiling point greater than 450° F., and a vapor pressure at room temperature less than 0.001 mm. Hg. Its solubility in water at room temperature is in the range of from 3% to 7%, which makes this characteristic about optimum for the purpose of the invention.

Although the slow-solubility penetrant compositions for use in the invention may be formulated from any of the liquid vehicles which are described and claimed in my U.S. Pat. Nos. 3,896,664, 3,929,664, and 3,930,407, I have found that a preferred liquid vehicle is the substance 2,2,4-trimethyl-1,3-pentanediol-diisobutyrate.

The objects of the invention may be achieved by use of the following formulation in which the relative content of ingredients are stated in weight percentages.

EXAMPLE I

Low-solubility liquid — zero to 94.8%
Indicator dye — .2% to 30%
Solvency accelerator — 5% to 99.8%

EXAMPLE II

An inspection penetrant having a so-called "Level 3" sensitivity and a mid-range degree of solubility acceleration is provided by the following formulation:
2,2,4-trimethyl-1,3-pentanediol-diisobutyrate — 27.5 gallons
ethylene glycol hexyl ether 27.5 gallons
Fluorescent dyes:
  C.I. Brightening Agent 68 — 3 lbs.
  C.I. Solvent Yellow 43 — 1.5 lbs.

In the above formulation, the ethylene glycol hexyl ether content may have any value from about 2 gallons up to 55 gallons, while the 2,2,4-trimethyl-1,3-pentanediol-diisobutyrate content may have corresponding values ranging from 53 gallons down to zero. Also, the color-former dye, C.I. Solvent Yellow 43 may be varied from as little as about 0.5 lb. up to as much as 3 lbs. and as long as the content of the C.I. Brightening Agent 68 is held constant at 3 lbs., the penetrant formula will still exhibit the desired "Level 3" sensitivity performance. Similar penetrant formulations may be prepared in which the dye-performance sensitivity is adjusted to a different desired level, merely by adjusting the concentration of the C.I. Brightening Agent 68 in accordance with known practices.

EXAMPLE III

An inspection penetrant having a so-called "Level 7" sensitivity and a high degree of "see-ability contrast" is provided by the following formulation:
2,2,4-trimethyl-1,3-pentanedioldiisobutyrate — 14 gallons
Diethylene glycol butyl ether acetate — 41 gallons
Fluorescent dyes:
  C.I. Brightening Agent 68 — 16 lbs.
  C.I. Solvent Yellow 43 — 2 lbs.

In the above formulation, the proportional concentration of the solubility accelerator (Diethylene glycol butyl ether acetate) may be varied from as little as 5% up to more than 94%, but the stated concentration of about 75% yields an optimum condition of washability from test parts and a maximum condition of see-ability contrast.

Formulations which are prepared in accordance with the above-given examples are characterized by relatively easy wash-removal of unwanted porosity background indications. They are readily recoverable from wash water containing dissolved penetrant, either by direct distillation of the wash water or by solvent-extraction into a halocarbon solvent followed by distillation of the halocarbon solvent, as described and claimed in my U.S. Pat. No. 3,926,044.

The penetrant formulations of the invention are particularly advantageous for use in penetrant testing and inspection for crack defects in objects having highly porous surfaces. For example, certain kinds of jet engine turbine blades and vanes have thin heat-resistant coatings on their air-foil surfaces, and such coatings are formed from a metallized spray which is oxidized by heat-treatment, leaving a heat-resistant but sponge-like coating. Quite often, minute craze cracks or shrinkage cracks may develop in critical areas of such turbine blades, and these cracks may extend through and/or below the porous heat-resistant surface.

I have devised measurment techniques for evaluating the equivalent magnitudes of surface porosity conditions and of cracks which may be found in failure-critical test parts, and I have devised a "Fractured Glass Test Panel", described and claimed in my above-identified U.S. Pat. No. 3,927,551, which permits the evaluation of a given inspection penetrant with respect to its ability to reveal crack indications in the presence of severe background porosity conditions. Evaluation of the penetrant compositions of the invention by use of this Fractured Glass Testing Panel shows that these compositions are characterized by extremely high values of see-ability contrast, and that porosity indications in the range of 10 microns or less can be effectively suppressed.

It turns out that many jet-engine turbine blades and vanes have surface porosity conditions in which the equivalent magnitude of the porosities is in the range of 10 microns or more. At the same time, actual crack defects may have equivalent magnitudes of 10 microns or less. Thus, the porosities may be as large or larger than the crack defects which are sought, the only difference being that the crack defects usually have a geometrical configuration which is different from the porosities, being deeper than the porosities, or having a linear character which may show up against a uniform porosity background. The penetrant compositions of the invention have the capability of selective suppression of unwanted porosity entrapment indications, while retaining penetrant entrapments and indications in actual cracks.

The pentrant compositions of the invention are also adaptable to the so-called I.D.E.A. technique of selective removal of background entrapments which is described and claimed in my above-identified U.S. Pat. No. 3,931,733. The I.D.E.A. technique refers to a procedure of "Interim-Drying Equilibrium Augmentation" of the solvency of surface porosity entrapments. Surface entrapments of penetrant are affected by this interim-dry operation to a much greater extent than are deeper crack entrapments, with the result that porosity entrapments are selectively removed, leaving crack entrapments relatively unaffected.

It will be understood that the penetrant compositions of the invention may be utilized under various conditions of wash-water temperature and with various methods of wash-water application. For example, wash-water temperatures may range from room temperature up to as much as 130° or more, although the preferred temperature is about 100° to 110° F. With regard to methods of washing of test parts, any suitable method may be employed, such as continuous spray, agitated soak, or simple dipping in a wash tank.

Also, it will be understood that the indicator dye of Example I may be either visible-color, fluorescent, a combination of visible-color and fluorescent, or ultraviolet absorbor, in accordance with known practices.

Finally, it will be understood that the solvency accelerator material may be the major constituent or even the only constituent in the liquid vehicle which is employed in the compositions of the invention, although for most applications mixtures of a low-solubility liquid vehicle and a solvency accelerator will be found most suitable.

It will be seen from the foregoing specification that I have devised a new and novel improvement in inspection penetrant compositions of the slow-solubility-type and process therefor, which permits a controlled enhancement of water solubility. Although the invention has been described with reference to particular embodiments thereof, it will be understood that various changes may be made therein without departing from the spirit of the invention or the scope of the appended claims.

I claim:

1. In a water-washable inspection penetrant process in which a slow-solubility-type water-removable dyed liquid inspection penetrant is applied to a test surface, excess surface penetrant is removed by washing said test surface with water, leaving entrapments of penetrant in any crack defects which are present, and said test surface is inspected for the presence of flaw indications, the improvement wherein said slow-solubility-type penetrant consists essentially of the following formulation, stated in weight percentages:

2,2,4-trimethyl-1,3-pentanediol-diisobutyrate — 94% to 5%

Diethylene glycol butyl ether acetate — 5% to 94%

C.I. Brightening Agent 68 — 0.7% to 3.64%

C.I. Solvent Yellow — 0.3% to 0.46%

* * * * *